(12) United States Patent
Kiwa et al.

(10) Patent No.: US 8,300,223 B2
(45) Date of Patent: Oct. 30, 2012

(54) MEASUREMENT DEVICE FOR THE DISTRIBUTION OF CHEMICAL CONCENTRATION

(75) Inventors: Toshihiko Kiwa, Okayama (JP); Keiji Tsukada, Okayama (JP)

(73) Assignee: National Univeristy Corporation Okayama Univeristy, Okayama (JP)

( * ) Notice: Subject to any disclaimer, the term of this patent is extended or adjusted under 35 U.S.C. 154(b) by 391 days.

(21) Appl. No.: 12/738,069

(22) PCT Filed: Oct. 10, 2008

(86) PCT No.: PCT/JP2008/068478
§ 371 (c)(1),
(2), (4) Date: Apr. 14, 2010

(87) PCT Pub. No.: WO2009/051080
PCT Pub. Date: Apr. 23, 2009

(65) Prior Publication Data
US 2010/0220327 A1    Sep. 2, 2010

(30) Foreign Application Priority Data
Oct. 15, 2007    (JP) ................................ 2007-268413

(51) Int. Cl.
G01N 21/00    (2006.01)
B01D 1/00    (2006.01)
B01D 1/30    (2006.01)
B01D 11/04    (2006.01)
C10G 21/00    (2006.01)
(52) U.S. Cl. ......................................... 356/432; 23/306
(58) Field of Classification Search ........... 356/432–444
See application file for complete search history.

(56) References Cited

U.S. PATENT DOCUMENTS
7,869,036 B2 *    1/2011    Kajiki et al. .................. 356/328
(Continued)

FOREIGN PATENT DOCUMENTS
JP    2002-350383    4/2002
(Continued)

OTHER PUBLICATIONS
Junichi Kondo et al., "Development of Laser Terahertz Emission pH-sensor Systems," *The 2007 Meeting Record I.E.E. Japan*, vol. 2007, No. 3, Mar. 15, 2007, p. 226.

(Continued)

*Primary Examiner* — Gregory J Toatley
*Assistant Examiner* — Jarreas C Underwood
(74) *Attorney, Agent, or Firm* — Sterne, Kessler, Goldstein & Fox, P.L.L.C.

(57) ABSTRACT

A material distribution measuring device (1) for measuring a reaction distribution or a concentration distribution of a material contained in a solution. The material distribution measuring device (1) comprises a material detecting plate (5) comprising a material-sensitive film (21) provided on an insulator (22) provided on a semiconductor (23), a flow passage forming part (6) forming a solution flow passage (12) on the material detecting plate (5), means for stabilizing the potential of the solution, means for applying a pulsed laser beam (9) from the semiconductor (23) side to the flow passage (12) side, means for scanning the material detecting plate (5) two-dimensionally with use of the pulsed laser beam (9), means for measuring the amplitude strength of pulsed electromagnetic waves generated upon the application of the pulsed laser beam (9) to the material detecting plate (5), and means for obtaining a reaction distribution or a concentration distribution of the material contained in the solution within the flow passage by qualitatively or quantitatively measuring the material to be detected from the amplitude strength.

3 Claims, 14 Drawing Sheets

U.S. PATENT DOCUMENTS 7,949,480 B2 * 5/2011 Parilov et al. .................. 702/40

FOREIGN PATENT DOCUMENTS

| JP | 2004-294087 | 10/2004 |
| JP | 2006-024774 | 1/2006 |
| JP | 2007-064700 | 3/2007 |
| JP | 2007-078621 | 3/2007 |

OTHER PUBLICATIONS

T. Kiwa et al., "Noncontact chemical sensor plate using terahertz wave emission and development system," *Extended Abstracts* (*The 54th Spring Meeting, 2007*); *The Japan Society of Applied Physics and Related Societies*; Mar. 22, 2007, p. 1181.

Masatsugu Yamashita et al., "Observation of Integrated Circuits by Laser-terahertz Emission Microscope." *The Japanese Society for Laser Microscopy*, Jul. 3, 2004, pp. 6-10.

Toshihiko Kiwa et al., "A Terahertz Chemical Microscope to Visualize Chemical Concentrations in Microfluidic Chips," *Japanese Journal of Applied Physics*, vol. 46, No. 44, pp. L1052-L1054, (2007).

Ja-Yu Lu et al., "Terahertz Microchip for Illicit Drug Detection," *IEEE Photonics Technology Letters*, vol. 18, No. 21, Nov. 1, 2006, pp. 2254-2256, (2006).

T. Ohkubo et al., "Micro-strip-line-based sensing chips for characterization of polar liquids in terahertz regime," Applied Physics Letters, vol. 88, May 22, 2006, pp. 212511-1-212511-3.

International Search Report for International Application No. PCT/JP2008/068478, Japanese Patent Office, mailed Jan. 13, 2009, 2 pgs.

T. Yoshinobu "Chemical Imaging Sensor and its Application to Biological Systems," Electrochimica Acta, 2001, pp. 259-263.

* cited by examiner

L=1000nm

L=650nm

L=200nm

L=150nm

MEASUREMENT DEVICE FOR THE DISTRIBUTION OF CHEMICAL CONCENTRATION

BACKGROUND OF THE INVENTION

1. Field of the Invention

The present invention relates to a measurement device for the distribution of chemical concentration in the solution. The device consist of a semiconductor and a material-sensitive film that a pulsed laser beam is irradiated and electromagnetic waves generated in the semiconductor is detected so as to detect whether a material to be detected exists in a solution or not. In detail, the present invention relates to a device for detecting reaction distribution or concentration distribution of a material present within a microflow channel for a chemical reaction in the solution.

2. Background Art

Conventionally, as a device for detecting a material in a solution, there is a sensor with a field-effect transistor. The sensor with the field-effect transistor generally includes (1) a sensitive film provided on a gate electrode of the field-effect transistor, (2) a sensor readout circuit reading out a signal from a drain electrode and a source electrode, (3) a power source for driving the sensor, and (4) a reference electrode for stabilizing electric potential of the solution.

In the sensor with the field-effect transistor constructed as the above, when a material to be detected included in a solution touches the sensitive film, the material is decomposed by catalysis of the sensitive film so that pH of the solution is changed. Then, a current of a local electric field of a semiconductor in the field-effect transistor changed by the change of pH is detected as a signal with the drain electrode and the source electrode.

There is provided a method for detecting a plurality of materials by arraying such sensors with field-effect transistors (sensor elements) on the same substrate (for example, see the Patent Literature 1).

The Patent Literature 1 describes a method for producing 100 pairs of sensor elements on a substrate of 50 mm×60 mm by patterning with photoresist.

The Patent Literature 2 describes a p-channel field-effect transistor and a sensor therewith that enzyme is directly fixed to a surface of a FET channel (a surface of a diamond) so as to improve sensitivity of the enzyme.

The Patent Literature 3 describes a method and device for failure diagnosis of a semiconductor device which can perform failure diagnosis under no bias with a pulsed laser beam without applying bias voltage on a chip (semiconductor device).

Furthermore, as a material detecting device with a laser beam, there is known a LAPS (Light-Addressable Portentiometric Sensor) (for example, see the Non-patent Literature 1). The LAPS includes a semiconductor silicon substrate and a sensor substrate, which includes an oxide film and a nitride film formed on the semiconductor silicon substrate, and is used, for example, as a sensor for measuring pH of a solution touching the sensor substrate.

An energy band curves in the interface between the semiconductor silicon substrate and the sensor substrate, and the curve also depends on pH of the solution touching the sensor substrate. As a result, width of a depletion layer in the interface between the semiconductor silicon substrate and the sensor substrate changes, whereby a current flowing at the time of irradiating a laser beam (photocurrent) changes.

As mentioned above, the current flowing at the time of irradiating the laser beam (photocurrent) is influenced by the change of width of the depletion layer at the point to which the beam is irradiated.

Detecting devices and detecting methods for detecting a material in a microflow passage have been examined. For example, as a detecting device for a material with surface plasmon, there is known a sensor with a SPR (surface plasmon) sensor. The SPR sensor is used with a method that a beam is irradiated to a floor surface of the microflow passage at a fixed angle and a spectrum of the total reflection beam is used for analysis.

Patent Literature 1: the Japanese Patent Laid Open Gazette 2002-350383

Patent Literature 2: the Japanese Patent Laid Open Gazette 2004-294087

Patent Literature 3: the Japanese Patent Laid Open Gazette 2006-24774

Non-patent Literature 1: T. Yoshinobu et al., Electrochimica Acta, Vol. 47 (2001) pp. 259-263

BRIEF SUMMARY OF THE INVENTION

Problems to be Solved by the Invention

In a method of arraying sensor elements such as disclosed in the Patent Literature 1, a working electrode and a counter electrode must be provided for each of the sensor elements, whereby the manufacturing process is complicated.

Furthermore, a signal wire for reading out a signal and a sensor driving circuit must be provided for each of the sensor elements.

In a p-channel field-effect transistor and a sensor therewith such as disclosed in the Patent Literature 2, ISFET structure must be provided for each material. Voltage must be applied on a semiconductor so as to make a current flow. Especially, measurement at an optional position is difficult.

In a method for failure diagnosis of a semiconductor device such as disclosed in the Patent Literature 3, a pulsed laser beam is directly irradiated to the semiconductor device so as to diagnose the semiconductor device itself. Then, it is difficult to apply such a method to a material to be detected except the semiconductor device which is easily affected by the laser beam, for example a biomaterial.

On the other hand, in the LAPS, electric characteristics of the silicon substrate in a current route between the position to which the laser beam is irradiated and an electrode which extracts photocurrent changes corresponding to the position, whereby proofreading of signal must be performed previously.

In the above-mentioned method with SPR, temperature management, shading of external light and the like are required. Furthermore, an optical system must be assembled and set accurately, whereby the cost of device for optical scan is huge.

In view of the conventional conditions, the inventors perform research and development so as to provide a device for detecting a reaction distribution or a concentration distribution of a material present within a microflow passage for a solution chemical reaction, thereby providing the present invention.

Means for Solving the Problems

A solution concentration distribution measuring device according to the present invention comprises:
　a material detecting plate including:
　　an insulator;
　　a semiconductor which touches one of end surfaces of the insulator and has predetermined thickness; and
　　a material-sensitive film which touches the other end surface of the insulator;
　a flow passage forming part which forms a flow passage of the solution on the material detecting plate;
　means for stabilizing electric potential of the solution;
　means for irradiating a femtosecond laser from the semiconductor side to the flow passage side;
　means for making the femtosecond laser scan the material detecting plate two-dimensionally;
　means for measuring directly amplitude strength of a pulsed electromagnetic wave generated by irradiating the femtosecond laser to the material detecting plate with the means for the two-dimensional scanning; and
　means for measuring the material to be detected qualitatively and quantitatively based on the amplitude strength so as to obtain the reaction distribution or the concentration distribution of the material in the solution in the flow passage as a two-dimensional map,
　wherein the material-sensitive film constitutes a part of an inner wall of the flow passage, and the predetermined thickness of the semiconductor is optical infiltration length which is an inverse of optical absorption coefficient of the semiconductor.

A solution concentration distribution measuring device according to the present invention comprises:
　a material detecting plate including:
　　an insulator;
　　a semiconductor which touches one of end surfaces of the insulator and has predetermined thickness; and
　　a material-sensitive film which touches the other end surface of the insulator;
　a flow passage forming part which forms a flow passage of the solution on the material detecting plate;
　means for stabilizing electric potential of the solution;
　means for irradiating a femtosecond laser from the semiconductor side to the flow passage side;
　means for making the femtosecond laser scan the material detecting plate two-dimensionally;
　means for measuring directly amplitude strength of a pulsed electromagnetic wave generated by irradiating the femtosecond laser to the material detecting plate with the means for the two-dimensional scanning; and
　means for measuring the material to be detected qualitatively and quantitatively based on the amplitude strength so as to obtain the reaction distribution or the concentration distribution of the material in the solution in the flow passage as a two-dimensional map,
　wherein the material-sensitive film constitutes a part of an inner wall of the flow passage, and
　the predetermined thickness of the semiconductor is within a thickness area of the semiconductor determined based on relation of product of amplitude strength of the pulsed electromagnetic wave about the thickness of the semiconductor and spatial resolution which is the minimum interval detectable by resolving the material in the solution on space coordinates as the reaction distribution or the concentration distribution about the thickness of the semiconductor.

In the solution concentration distribution measuring device according to the present invention, the determined thickness area of the semiconductor corresponds to a range between a first inflection point and a second inflection point on a curve indicating the relation of the product of the pulsed electromagnetic wave about the thickness of the semiconductor and the spatial resolution of the reaction distribution or the concentration distribution about the thickness of the semiconductor.

Effect of the Invention

As the effect of the present invention, by irradiating the femtosecond laser which is the pulsed laser beam to the material detecting plate corresponding to the material-sensitive film (measurement part) constituting the part of the flow passage, the pulsed electromagnetic wave having the amplitude strength depending on the amount the material in the solution in the flow passage corresponding to the irradiated position efficiently, and by measuring the amplitude strength, quantitative evaluation detecting the existence of the material to be detected can be performed.

The thickness of the semiconductor included in the material detecting plate is within the range determined in consideration of the amplitude strength of the pulsed electromagnetic wave and the spatial resolution of the reaction distribution or the concentration distribution of the material in the measured solution, whereby the measurement accuracy of the solution concentration distribution measuring device can be maintained and the thickness of the semiconductor can be optimized so as to secure the spatial resolution.

Then, the material at an optional position in the flow passage can be measured with high resolution (not more than 1 μm). Accordingly, the continuous measurement of the whole flow passage is enabled, whereby the reaction distribution or the concentration distribution of the material in the measured solution can be surveyed.

The solution reaction and concentration distribution in a micro flow passage or TAS (Total Analysis System) can be detected non-destructive, non-contactly and real-timely. Especially, by using a femtosecond laser beam as the pulsed laser beam, the reaction of material can be measured real-timely.

Furthermore, in the case that the measurement is performed at an optional position in the flow passage so as to measure the pulsed electromagnetic wave generated at the irradiated position of the pulsed laser beam, accurate and quantitative measurement can be performed without proof-reading as the above-mentioned LAPS.

DETAILED DESCRIPTION OF THE INVENTION

Explanation will be given below on the best embodiment of the present invention referring attached drawings. Each of the parts common among the drawings is indicated by the same sign and duplicated explanation thereof is omitted.

Figure 1:
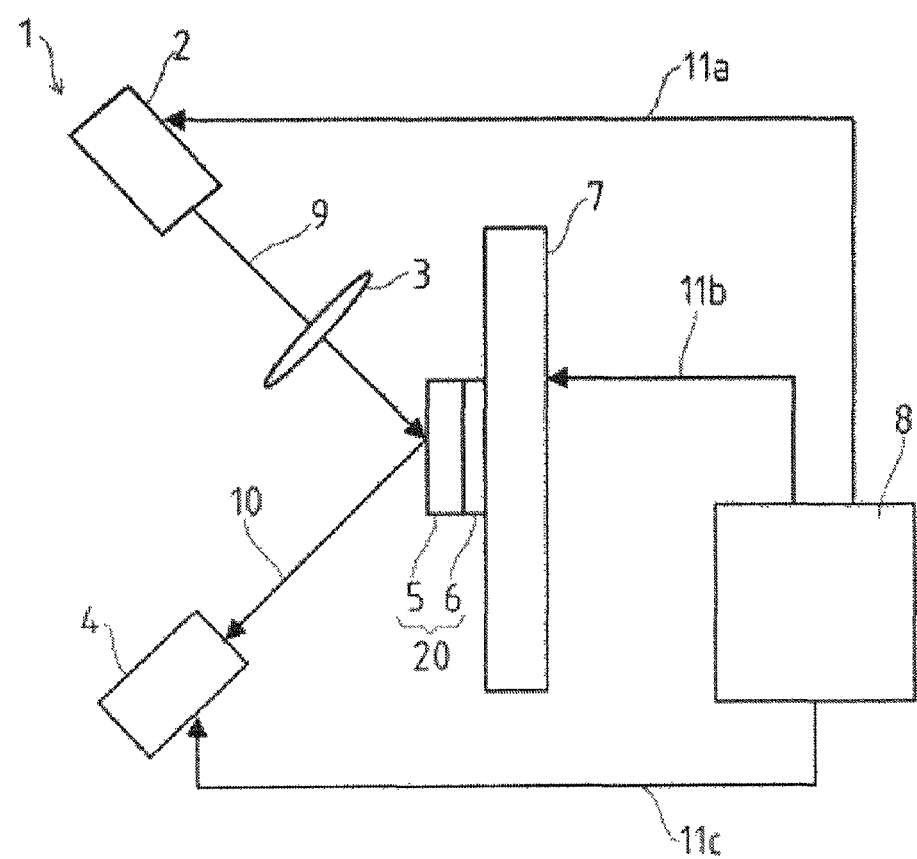
FIG. 1 It is a schematic drawing of a solution concentration distribution measuring device according to the present invention.
Figure 2:
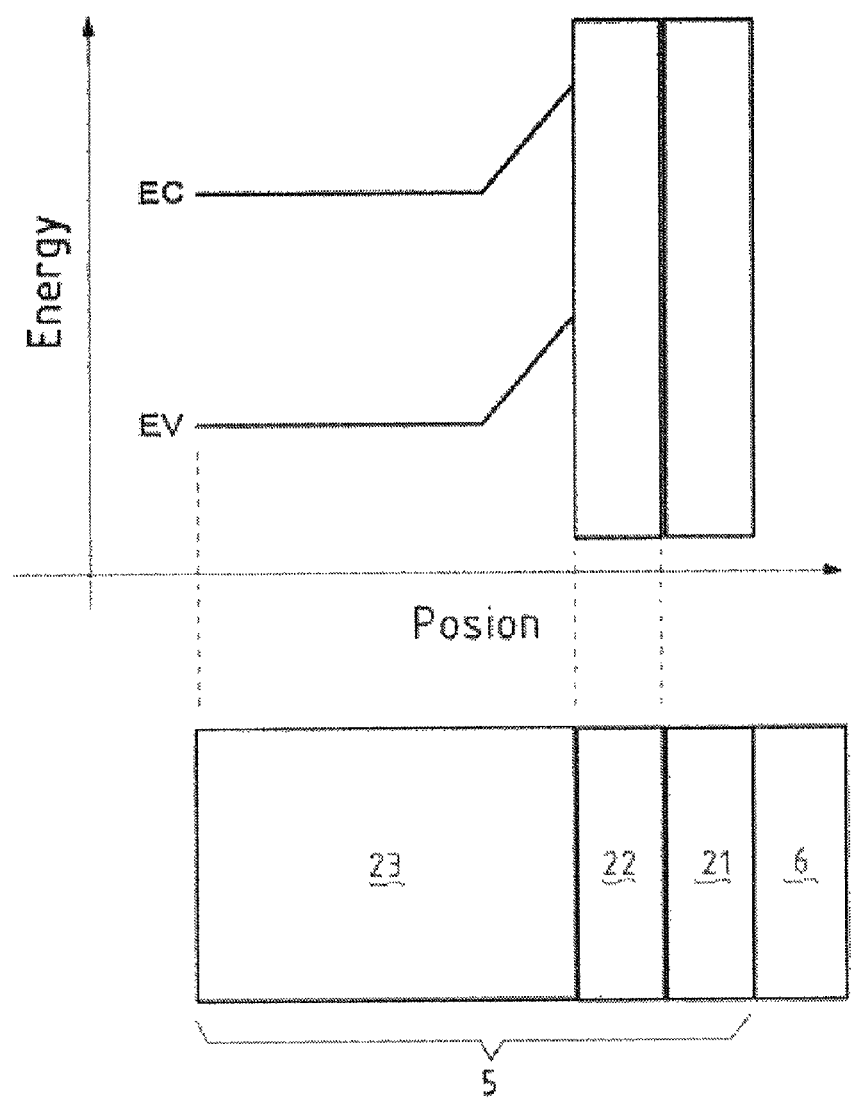
FIG. 2 It is a schematic diagram of distribution of energy bands of a material detecting plate according to the present invention.
Figure 3:
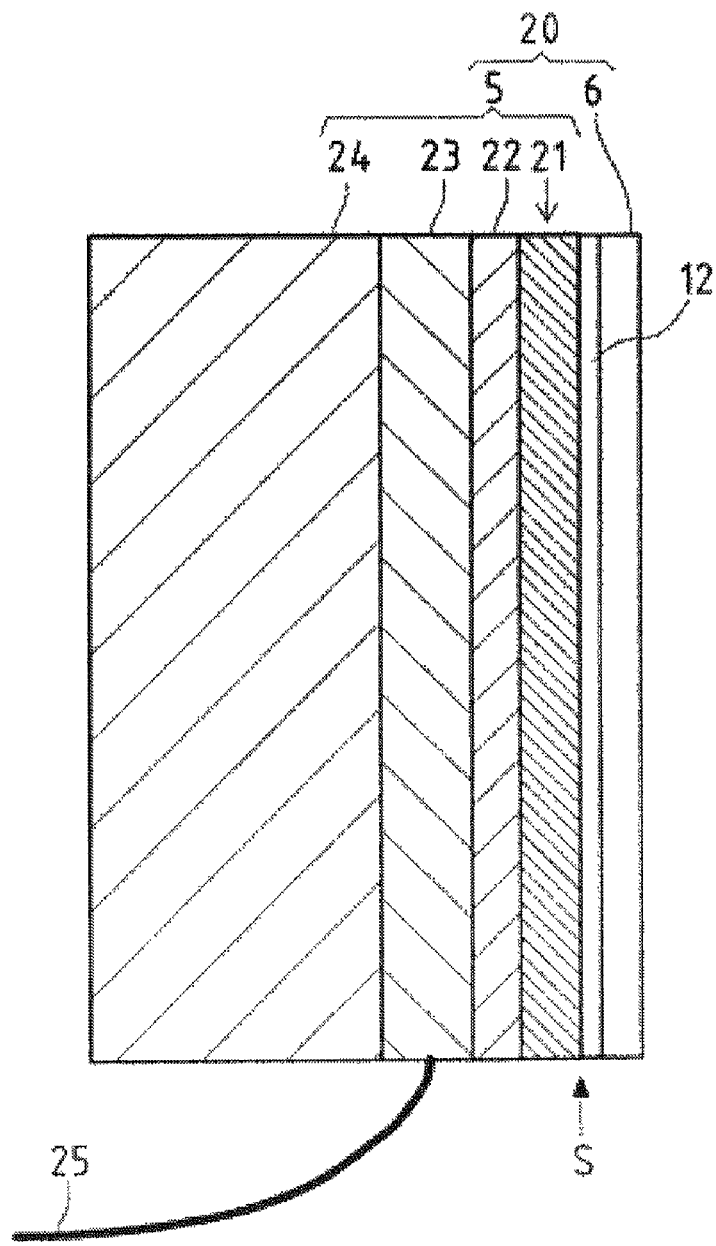
FIG. 3 It is a schematic drawing of the material detecting plate of the embodiment.
Figure 4:
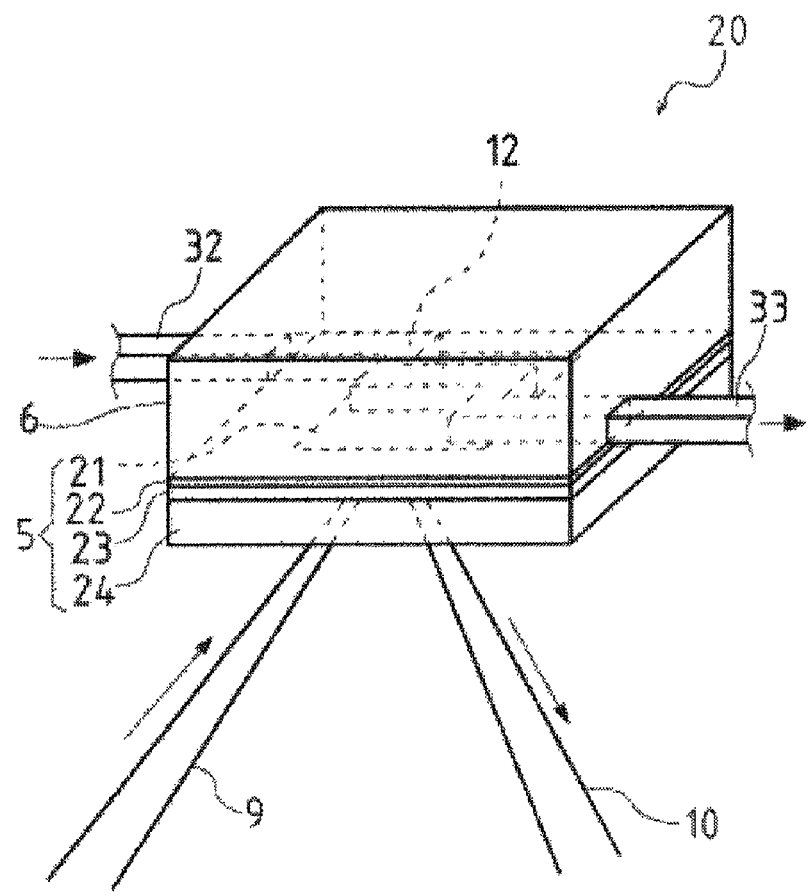
FIG. 4 It is a perspective view of a flow passage forming part and a flow passage.
Figure 5:
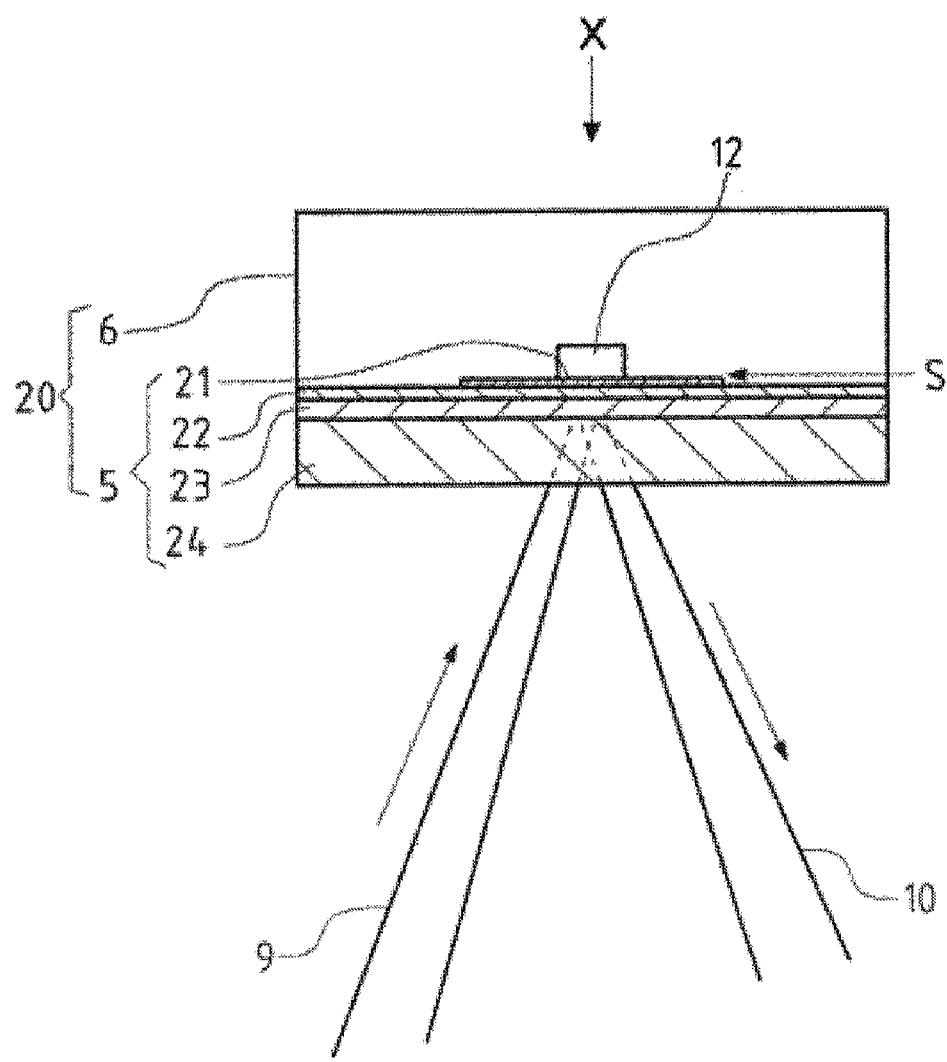
FIG. 5 It is a sectional view of the same.
Figure 6:
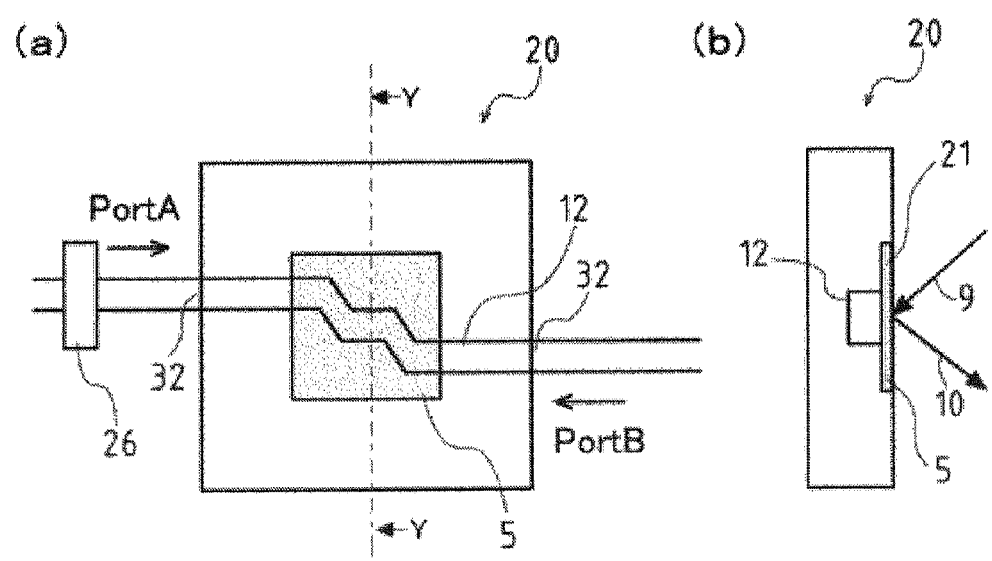
FIG. 6 It is a schematic drawing of a measurement area of the solution concentration distribution measuring device.
Figure 7:
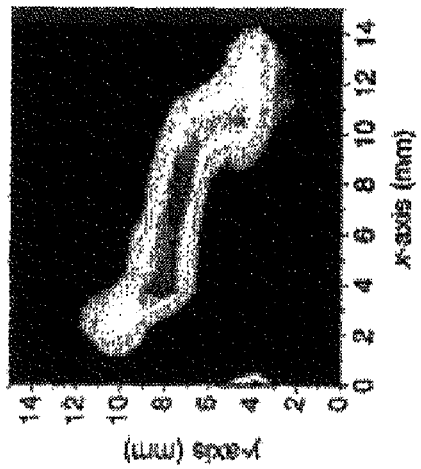
FIG. 7 It is a diagram of measurement results of pH concentration distribution.
Figure 7:
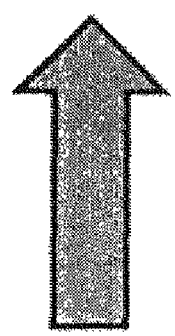
Figure 7:
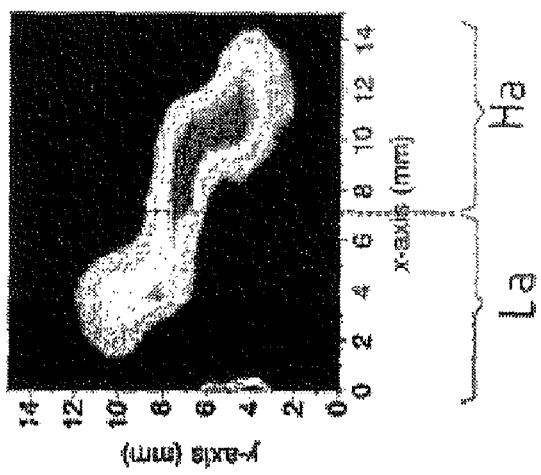
Figure 8:
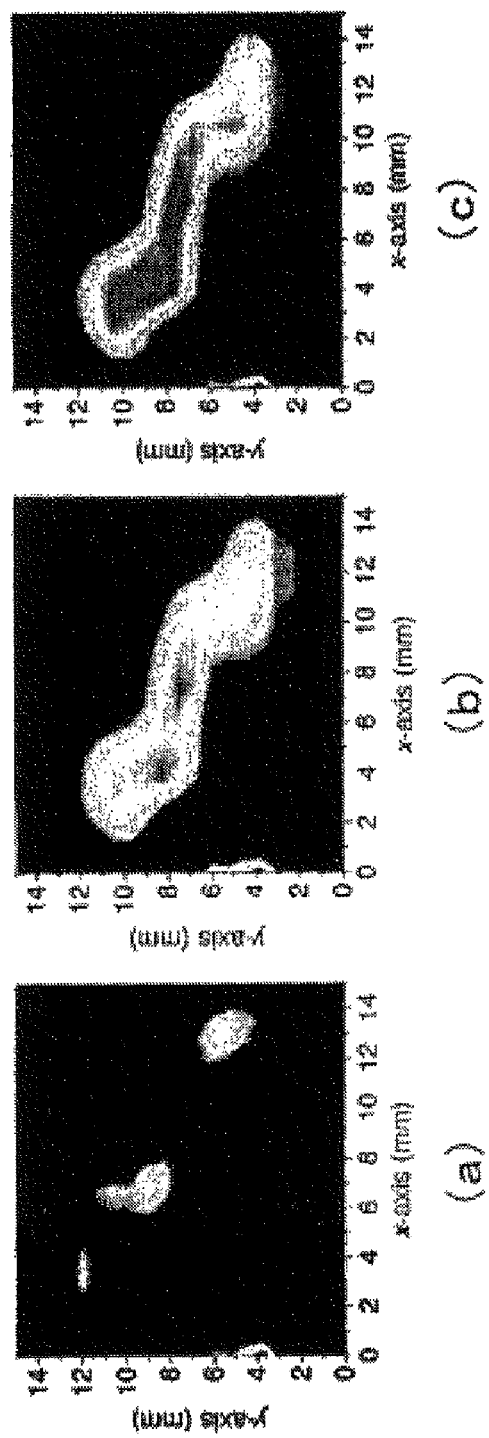
FIG. 8 It is a diagram of measurement results in the case that pH concentration distribution changes.
Figure 9:
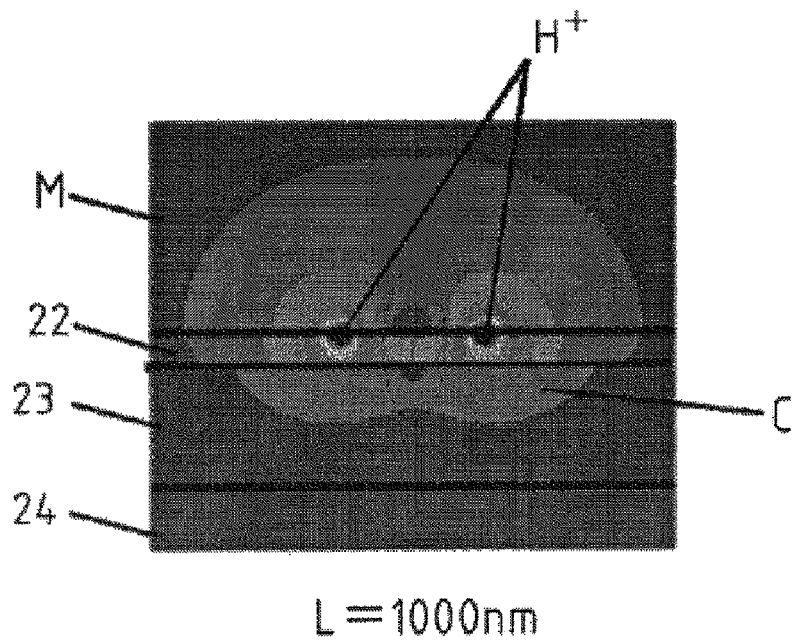
FIG. 9 It is a diagram of electric field distribution simulation in the sectional direction of the material detecting plate (L=1000 nm).
Figure 10:
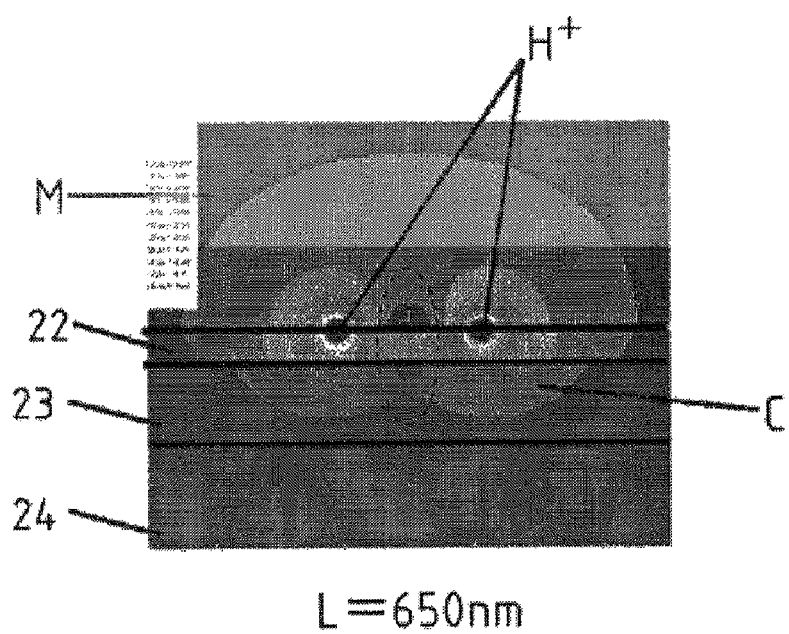
FIG. 10 It is a diagram of electric field distribution simulation in the sectional direction of the material detecting plate (L=650 nm).
Figure 11:
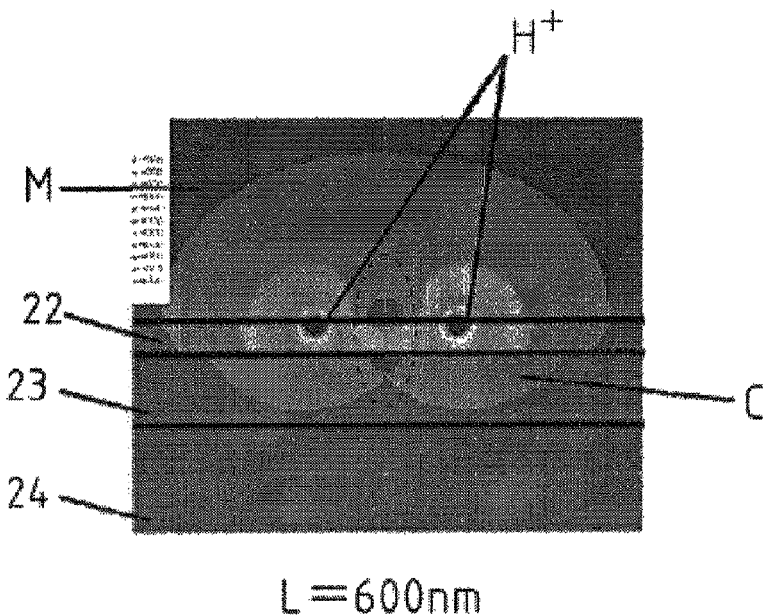
FIG. 11 It is a diagram of electric field distribution simulation in the sectional direction of the material detecting plate (L=600 nm).
Figure 12:
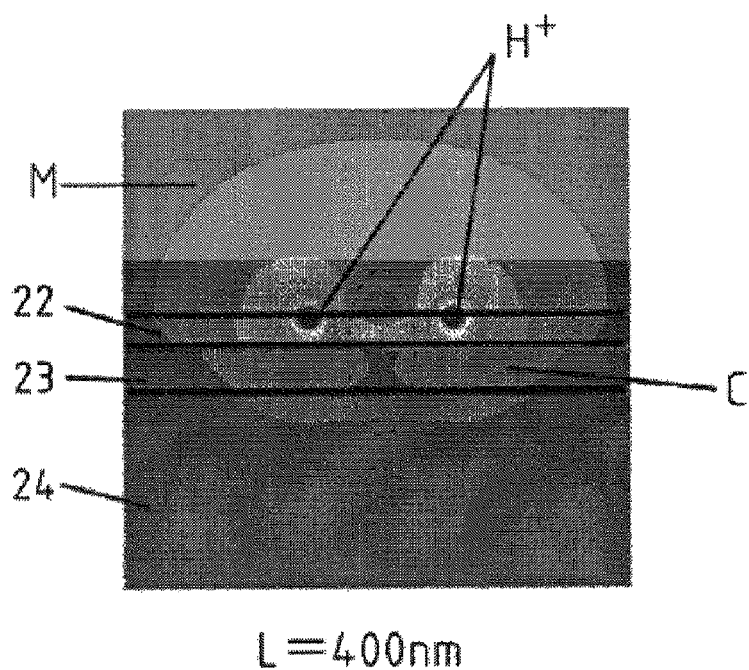
FIG. 12 It is a diagram of electric field distribution simulation in the sectional direction of the material detecting plate (L=400 nm).
Figure 13:
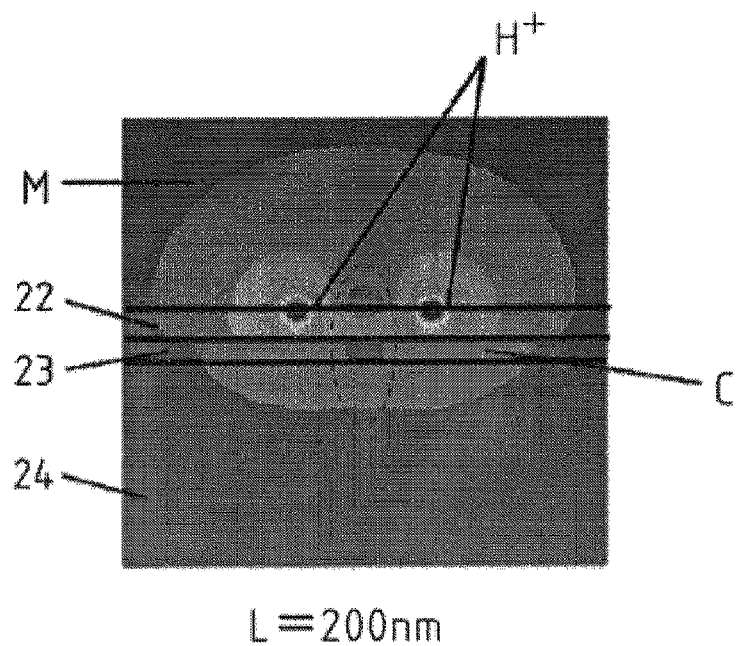
FIG. 13 It is a diagram of electric field distribution simulation in the sectional direction of the material detecting plate (L=200 nm).
Figure 14:
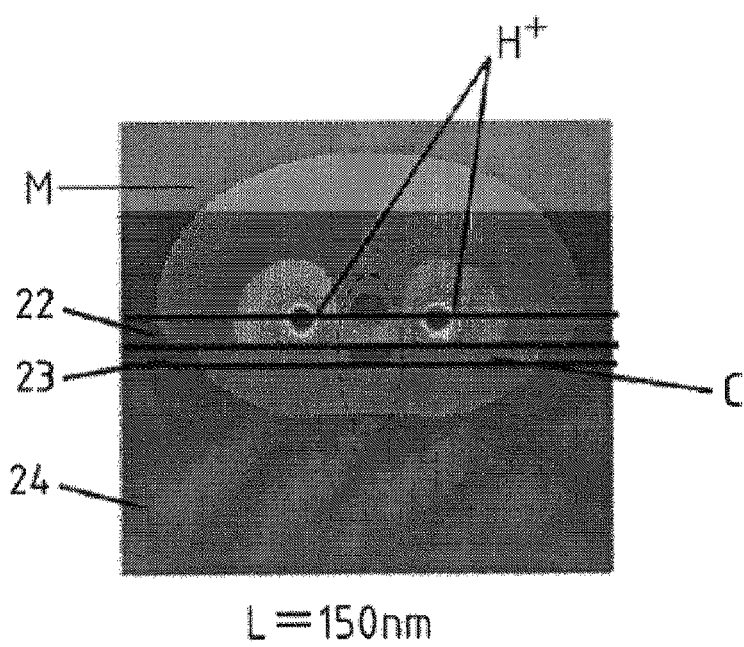
FIG. 14 It is a diagram of electric field distribution simulation in the sectional direction of the material detecting plate (L=150 nm).
Figure 15:
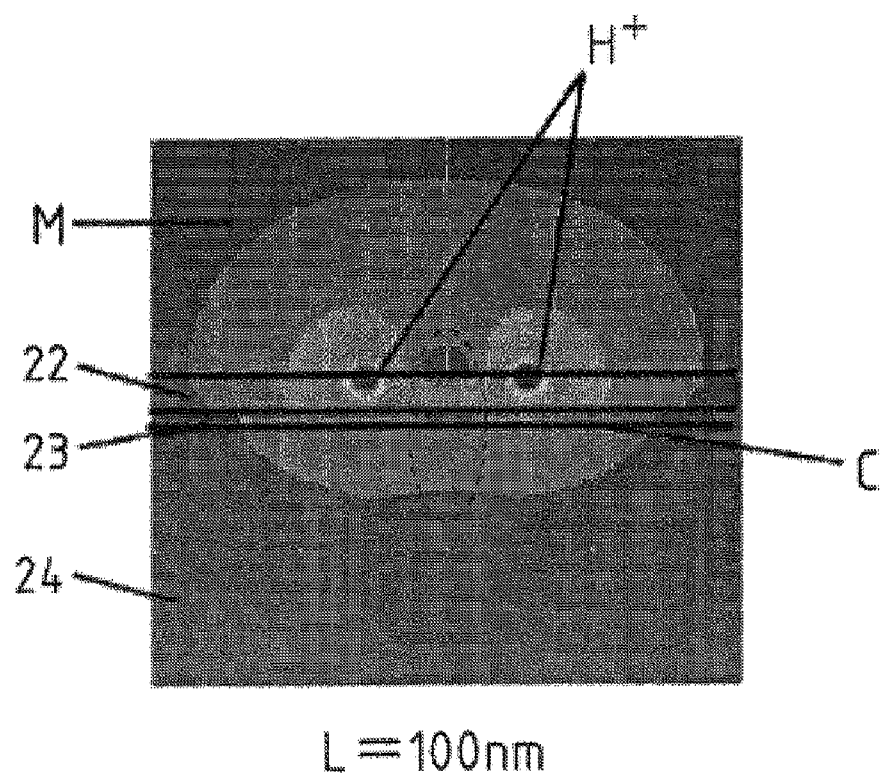
FIG. 15 It is a diagram of electric field distribution simulation in the sectional direction of the material detecting plate (L=100 nm).
Figure 16:
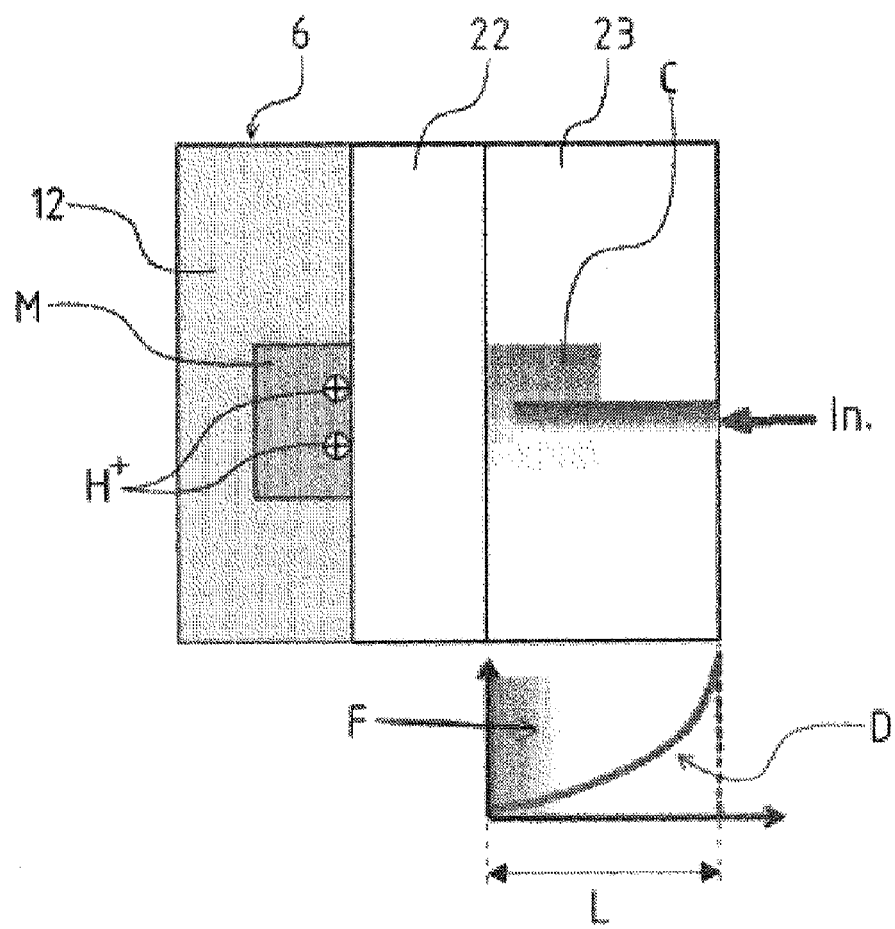
FIG. 16 It is a drawing of a detection principle of the material detecting plate.
Figure 17:
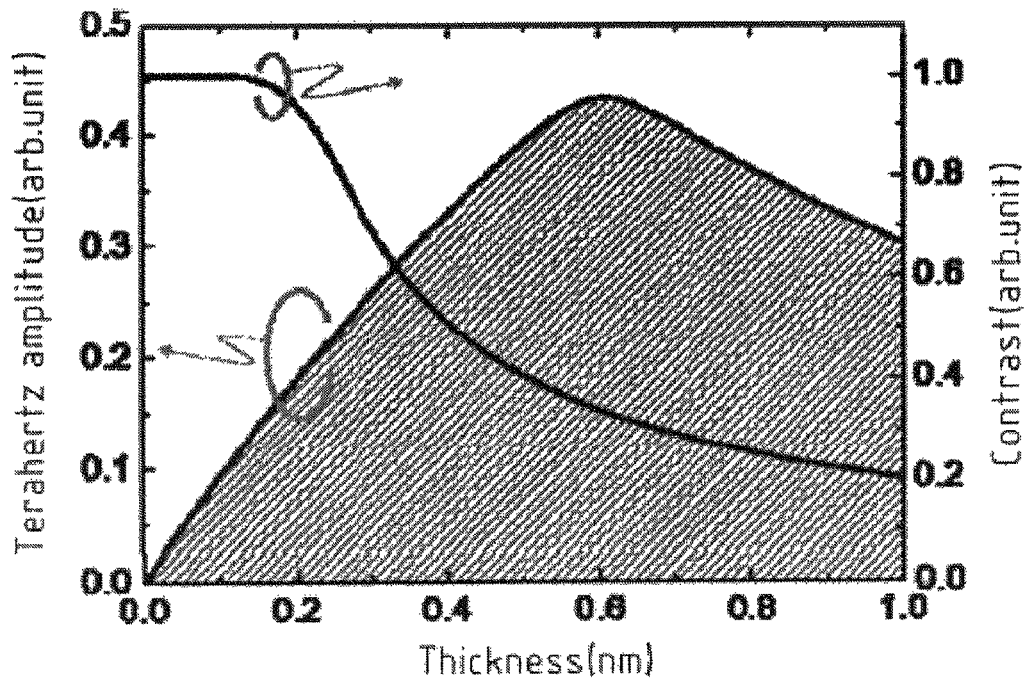
FIG. 17 It is a diagram of relation between thickness of a semiconductor and contrast and amplitude strength of terahertz wave.
Figure 18:
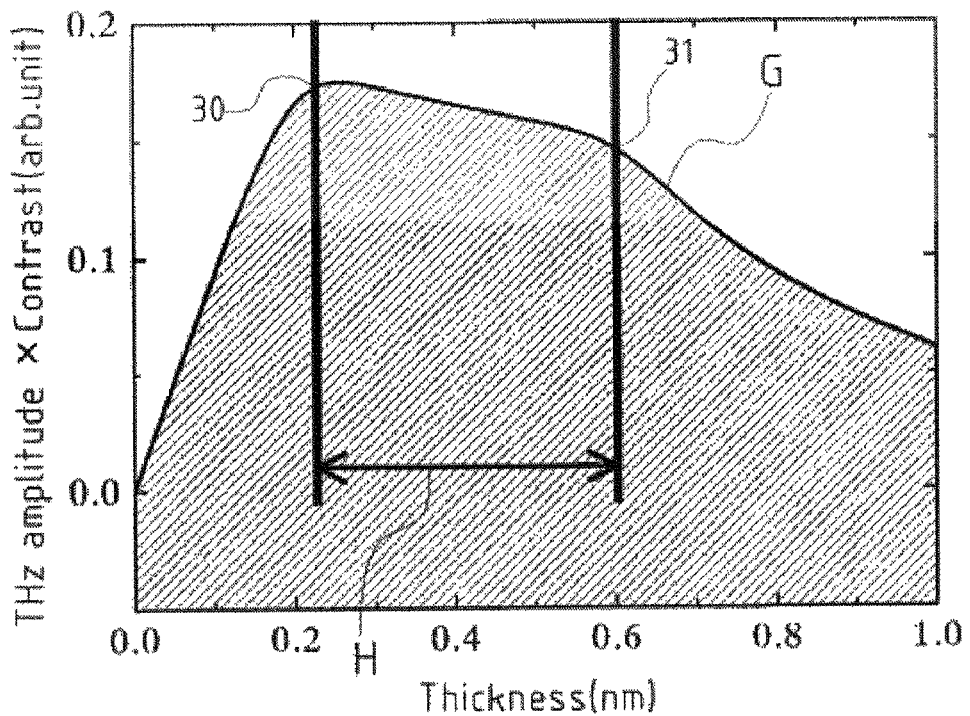
FIG. 18 It is a diagram of relation between the thickness of the semiconductor and the product of the contrast and the amplitude strength of terahertz wave.

FIG. 1 is a schematic drawing of a solution concentration distribution measuring device according to the present invention. FIG. 2 is a schematic diagram of distribution of energy bands of a material detecting plate according to the present invention. FIG. 3 is a schematic drawing of the material detecting plate of the embodiment. FIG. 4 is a perspective view of a flow passage forming part and a flow passage. FIG. 5 is a sectional view of the same. FIG. 6 is a schematic drawing of a measurement area of the solution concentration distribution measuring device. FIG. 6(a) is an arrow sectional view of the line X in FIG. 5, and FIG. 6(b) is an arrow sectional view of the line Y-Y in FIG. 6(a). FIG. 7 is a diagram of measurement results of pH concentration distribution. FIG. 7(a) is a diagram of measurement results of pH concentration distribution before stirring, and FIG. 7(b) is a diagram of measurement results of pH concentration distribution after stirring. FIG. 8 is a diagram of measurement results in the case that pH concentration distribution changes. FIG. 8(a) shows measurement results in the case that only air exists in the flow passage, FIG. 8(b) shows measurement results in the vicinity of pH 2, and FIG. 8(c) shows measurement results in the vicinity of pH 11. FIG. 9 is a diagram of electric field distribution simulation in the sectional direction of the material detecting plate (L=1000 nm). FIG. 10 is a diagram of electric field distribution simulation in the sectional direction of the material detecting plate (L=650 nm). FIG. 11 is a diagram of electric field distribution simulation in the sectional direction of the material detecting plate (L=600 nm). FIG. 12 is a diagram of electric field distribution simulation in the sectional direction of the material detecting plate (L=400 nm). FIG. 13 is a diagram of electric field distribution simulation in the sectional direction of the material detecting plate (L=200 nm). FIG. 14 is a diagram of electric field distribution simulation in the sectional direction of the material detecting plate (L=150 nm). FIG. 15 is a diagram of electric field distribution simulation in the sectional direction of the material detecting plate (L=100 nm). FIG. 16 is a drawing of a detection principle of the material detecting plate. FIG. 17 is a diagram of relation between thickness of a semiconductor and contrast and amplitude strength of terahertz wave. FIG. 18 is a diagram of relation between the thickness of the semiconductor and the product of the contrast and the amplitude strength of terahertz wave.

FIG. 1 shows an embodiment of a solution concentration distribution measuring device (material distribution measuring device) according to the present invention.

The solution concentration distribution measuring device 1 includes a material detecting plate 5 (sensing plate) that a material-sensitive film 21 is provided via an insulator 22 on a semiconductor 23, a flow passage forming part 6 which fauns a flow passage 12 in which a solution including a material to be detected flows, means for stabilizing voltage of the solution (reference electrode 26 discussed later), means for irradiating a pulsed laser beam 9 from the side of the semiconductor 23 opposite to the insulator 22 to the position of the material detecting plate 5 corresponding to the flow passage 12 so as to generate a pulsed electromagnetic wave 10 having amplitude strength depending on the amount of the material to be detected at the irradiated position (pulsed laser source 2), means for scanning two-dimensionally and irradiating the pulsed laser beam 9 (scanning table 7, pulsed laser source 2), means for measuring the amplitude strength of the pulsed electromagnetic wave 10 (detecting and exchanging unit 4), and means for measuring the material to be detected qualitatively or quantitatively based on the amplitude strength so as to obtain reaction distribution or concentration distribution of the material in the solution in the flow passage 12 (controlling and analyzing unit 8). Especially, in this embodiment, the material-sensitive film 21 discussed later constitutes a part of the inner wall of the flow passage 12 in the flow passage forming part 6 (in this embodiment, a bottom of the inner wall of the flow passage 12). Explanation will be given below on the details of principle and device construction.

In this embodiment, for convenience, the part of the inner wall of the flow passage 12 at the side of the material detecting plate 5 is referred to as the bottom.

Firstly, explanation will be given below on the principle of generation of electromagnetic wave with irradiation of laser pulse. When a laser beam having larger energy than a band gap is irradiated to a position in the semiconductor at which an electric field E exists, an electron-hole pair is generated by photoexcitation, and the electron-hole pair is accelerated by the electric field E so as to generate current. When the laser beam is continuous, the stationary current flows. However, when the laser beam is pulsed, the excited electron-hole pair is relaxed for certain fixed time and the current stops flowing, whereby the pulsed current flows depending on the width and relaxation time of the beam pulse. According to below formula (1) led from the Maxwell equations of classic electromagnetics, when temporal change occurs in the current flowing in the semiconductor, the electromagnetic wave is irradiated from the semiconductor.

[Formula 1]

$$\vec{E}_{emission} \propto \frac{\partial \vec{J}}{\partial t} \quad (1)$$

$$= \frac{\partial (n e \vec{v})}{\partial t}$$

$$= \frac{\partial (n e \mu \vec{E}_{local})}{\partial t}$$

In the formula (1), $E_{emission}$ indicates an electric field vector of the electromagnetic wave, J indicates a photocurrent density vector, n indicates density of the photoexcited electron-hole pair, e indicates elementary electric charge amount, v indicates drift velocity of the electron-hole pair accelerated by an electric field $E_{local}$ in the semiconductor at the position to which the beam is irradiated, and μ indicates mobility of electric charge.

According to the formula (1), the amplitude strength of the generated electromagnetic wave is proportional to the electric field $E_{local}$ in the semiconductor at the position to which the beam is irradiated.

Next, explanation will be given below on the reason of that the amplitude strength of the pulsed electromagnetic wave 10 generated from the semiconductor 23 by the irradiation of the pulsed laser beam 9 changes in the case that the material to be detected in the solution exists on the surface of the material detecting plate 5 provided on the semiconductor 23.

Firstly, when the solution including the material to be detected touches the material-sensitive film which senses specific material to be detected, hydrogen ion concentration of the solution changes. Namely, pH of the solution touching the material-sensitive film is changed.

For example, in the material-sensitive film including urease (enzyme), there is known that urea is hydrolyzed by catalysis so as to generate ammonia, whereby pH is raised.

FIG. 2 is a schematic diagram of distribution of energy bands of the material detecting plate. The axis of abscissa indicates the position, and the axis of ordinate indicates the energy. In the drawing, EC indicates a conduction band, and EV indicates a valence band. A depletion layer is formed at the boundary between the insulator 22 and the semiconductor 23. The depletion layer is an area in which no carrier exists, and the local electric field E is formed in the depletion layer. Then, the electric field exists stationarily in the depletion layer without applying voltage from the outside. When the beam is irradiated to the depletion layer so as to generate the electron-hole pair, the electromagnetic wave is generated according to the formula (1).

Herein, the direction and magnitude of the local electric field E may change corresponding to the state of the boundary between the insulator 22 and the semiconductor 23 or the characteristics of the semiconductor 23. However, the especial important point of the principle of generation of electromagnetic wave is that the local electric field E is formed.

As shown in FIG. 2, when the hydrogen ion concentration of the solution (pH of the solution) changes, the density of hydrogen ion and hydroxyl ion adsorbing to the material-sensitive film 21 changes. The electric charge in the surface of the material-sensitive film 21 changes so that the local electric field E in the depletion layer formed at the boundary between the insulator 22 and the semiconductor 23 changes, whereby the amplitude strength of the electromagnetic wave proportional to the local electric field E changes.

Accordingly, the amplitude strength of the electromagnetic wave generated by the irradiation of the pulsed laser beam 9 can be measured directly, whereby the material to be detected can be detected without forming an electrode reading out a signal for each material to be detected.

According to the above principle, the material to be detected is detected with the device construction shown in FIG. 1.

FIG. 1 is a schematic drawing of the solution concentration distribution measuring device in this embodiment. As shown in this drawing, the solution concentration distribution measuring device 1 in this embodiment has an irradiating unit, the detecting and exchanging unit 4 and the controlling and analyzing unit 8.

In FIG. 1, the irradiating unit includes the scanning table 7, the pulsed laser source 2 and a beam-condensing unit 3 and has a function of irradiating the pulsed laser beam 9 having predetermined wavelength to the specific position of the material detecting plate 5.

Furthermore, the irradiating unit has a function of irradiating the pulsed laser beam 9 for the two-dimensional scanning. Namely, the scanning means has a function of irradiating the pulsed laser beam 9 to the material detecting plate 5 while the material detecting plate 5 and the flow passage forming part 6 are reciprocated on the scanning table 7 (stage) with a driving unit (not shown).

As shown in FIG. 4, the pulsed laser beam 9 is irradiated to the semiconductor 23 corresponding to the position of the material-sensitive film 21 forming the bottom of the inner wall of the flow passage 12 (irradiated to the flow passage 12 at one of the side surfaces of the flow passage forming part 6). The scanning table 7 moves the material detecting plate 5 and the whole flow passage forming part 6 adhering to the material detecting plate 5 and laminated so that the semiconductor 23 corresponding to the material-sensitive film 21 at the bottom of the inner wall of the flow passage 12 is moved to the position to which the pulsed laser beam 9 is irradiated, whereby the laser beam irradiated surface of the semiconductor 23 is scanned. When the pulsed laser beam 9 is irradiated, the pulsed electromagnetic wave 10 is generated continuously from the laser beam irradiated position of the semiconductor 23.

The scanning construction is not limited to the construction in this embodiment, and may alternatively be constructed that the material detecting plate 5 is scanned two-dimensionally with the pulsed laser beam 9 by a mirror which is vibrated or rotated (not shown) or the like, or the beam is irradiated while the pulsed laser source 2 is rocked.

As shown in FIG. 1, in this embodiment, the plane formed by the routes of the pulsed laser beam 9 and the pulsed electromagnetic wave 10 is substantially horizontal, that is, FIG. 1 is a plan view and the routes of the pulsed laser beam 9 and the pulsed electromagnetic wave 10 form a substantially horizontal plane when viewed in side. However, the construction preferably set corresponding to the shape and fixing method of each unit and is not necessary to construct the substantially horizontal plane. The pulsed laser beam 9 is irradiated to one of the sides of the flow passage 12 (in this embodiment, the bottom side of the flow passage 12) included in the flow passage forming part.

The incident angle of the pulsed laser beam 9 to the material detecting plate 5 is preferably an angle at which the wavelength of the pulsed laser beam 9 is absorbed the most to the semiconductor 23 of the material detecting plate 5. However, corresponding to the shape and fixing method of each unit, the incident angle does not have to be limited to this angle and is not limited especially.

Preferably, the pulsed laser source 2 is a mode-locked titanium sapphire laser or a femtosecond fiber laser which can generate the pulsed laser beam 9. Preferably, the wavelength of the pulsed laser beam 9 is within the range not less than 300 nm (=0.3 μm) and not more than 2 μm, the time-average energy is not less than 0.1 mW and not more than 10 W, and the pulse width is not less than 1 femtosecond (1 fs=0.001 ps) and not more than 10 picoseconds (10 ps).

Namely, in case of the excitation of electromagnetic wave, by using the pulsed laser beam 9 with small width of time as a light source, the electromagnetic wave can be excited without largely affecting the semiconductor 23 and the solution. Especially, by using the femtosecond laser beam as the pulsed laser beam 9, time-resolved measurement with high time resolution is enabled, whereby the reaction of material can be measured real-timely. The maximum beam pulse width with which the semiconductor 23 and the solution are not affected thermally can be estimated to be about 10 picoseconds. By using the femtosecond laser, even if the solution is minute amount, the influence of heating with the laser can be held down to the minimum so as to suppress thermal destruction of the sample.

In FIG. 1, the detecting and exchanging unit 4 is for example an electromagnetic wave detecting bolometer or a semiconductor optical switch, and detects the pulsed electromagnetic wave 10 radiated from the irradiated position of the pulsed laser beam 9 and exchanges it into a voltage signal which changes temporarily corresponding to the temporal waveform of electric field amplitude of the electromagnetic wave. The component included in the pulsed electromagnetic wave 10 is within the range from 10 GHz to 100 THz, whereby the detecting and exchanging unit 4 of general construction can be used. In the construction of the solution concentration distribution measuring device 1 according to the present invention, the terahertz area is more preferable than the gigahertz area as the pulsed electromagnetic wave 10. In the case of using the terahertz area, differently from the case of using the gigahertz area, the electromagnetic wave can be guided to the detector easily with optical methods using a mirror, lens, and the like. On the other hand, the area with higher frequency than the terahertz area is so-called light. However, in the case of using the light, means for distinguishing circumjacent light from the light of signal must be provided so that the device is complicated, whereby the electromagnetic wave of the terahertz area is more preferable than the electromagnetic wave of the area with higher frequency than the terahertz area such as the light.

The controlling and analyzing unit 8 performs detection of existence of the material to be detected (qualitative measurement), quantitative measurement of the material to be detected, and analysis such as reaction distribution and concentration distribution of the material to be detected based on the voltage signal exchanged in the detecting and exchanging unit 4. In this embodiment, the controlling and analyzing unit 8 is a computer for enabling execution of the control and analysis explained in this specification, and, in addition, controls the scanning table 7, the detecting and exchanging unit 4 and the pulsed laser source 2 via control signal lines 11 (11a, 11b, 11c).

FIG. 3 is a schematic drawing of the material detecting plate 5. The material detecting plate 5 has the material-sensitive film 21, the insulator 22, the semiconductor 23 and a transparent substrate 24 constituting the bottom of the flow passage 12. Namely, the material detecting plate 5 has the insulator 22, the semiconductor 23 which touches one of the end surfaces (in FIG. 3, left end surface) of the insulator 22 and has predetermined thickness, and the material-sensitive film 21 which touches the other end surface (in FIG. 3, right end surface) of the insulator 22. The material detecting plate 5 and the flow passage forming part 6 constitute a measurement plate 20.

In the case of measuring only pH of the solution, the material-sensitive film 21 is not necessary. A film to which enzyme is fixed is provided as the material-sensitive film 21. Accordingly, in the case that the material to be detected which reacts to the enzyme exists in the solution, pH is changed by the reaction of the enzyme and the material to be detected, whereby the amplitude strength of the pulsed electromagnetic wave 10 generated at the position at which the material-sensitive film 21 exists changes. By picking up the change of the amplitude strength, the material to be detected can be detected. Accordingly, the material-sensitive film 21 includes the enzyme so that the distribution can be detected by the enzyme reaction with the material detecting plate 5. Concretely, the material-sensitive film 21 is constructed by adding the enzyme to a light crosslinking agent and applying it on the bottom of the flow passage 12. Otherwise, a seat including the enzyme is stuck on the bottom of the flow passage 12.

A film to which an antigen is fixed is provided as the material-sensitive film 21. Accordingly, in the case that the material to be detected which reacts to the antigen (antibody) exists in the solution, the electric charge in the surface of the sensitive film is changed by the reaction of the antigen and the material to be detected (antibody), whereby the amplitude strength of the pulsed electromagnetic wave 10 generated at the position at which the material-sensitive film 21 exists changes. Based on the value of the changed amplitude strength (about the frequency), the material to be detected (antibody) can be detected. Accordingly, the material-sensitive film 21 includes the antigen so that the antibody corresponding thereto can be detected, whereby the solution concentration distribution measuring device 1 can be used as a so-called biological sensor.

The size of the material-sensitive film 21 at the bottom of the flow passage 12 (projected area to the semiconductor 23) is designed corresponding to the irradiation range of the pulsed laser beam 9. Namely, the size of the material-sensitive film 21 is designed larger than the irradiation range of the pulsed laser beam 9 (in this embodiment, the size of the material-sensitive film 21 is about 15 mm×15 mm. The size of the material-sensitive film 21 shown in FIG. 6 is the measurement area). In the size of the flow passage 12 provided on the material-sensitive film 21, the width is about 3 mm, the height is about 2 mm, and the length is about 18 mm (the length of flow passage on the material-sensitive film 21). Concretely, the area of the material-sensitive film 21 constituting the inner wall surface of the flow passage 12 is preferably not less than ¼ of the surface area of the inner wall of the flow passage 12. That is because the area for detecting the reaction distribution may be insufficient in the case that the area of the material-sensitive film 21 is less than ¼. The width of the flow passage 12 is preferably not more than ⅕ of the length thereof. That is because the thermal capacity is large the case that the width is more than ⅕ so that sudden heating and cooling are difficult, whereby the availability of the reaction with the micro flow passage is canceled.

As shown in FIG. 3, the film of the insulator 22 is formed on the semiconductor 23, and the material-sensitive film 21 is arranged on the film of the insulator 22 and at the bottom of the flow passage 12. In this embodiment, silicone oxide, silicone nitride or the like is used as the insulator 22. The thickness of the insulator 22 is about 220 nm and the thickness of the semiconductor 23 is about 150 nm. For obtaining large amplitude strength of the pulsed electromagnetic wave 10, the thickness of the semiconductor 23 is preferably equal to optical infiltration length determined based on the wavelength of the pulsed laser beam 9 and the type of the semiconductor 23. The optical infiltration length is the inverse of optical absorption coefficient about the semiconductor 23. For example, in the case that the wavelength of the pulsed laser beam 9 is 790 nm and the semiconductor 23 is silicon with high resistance, about 2 micron of the thickness of the semiconductor 23 make the generation of the pulsed electromagnetic wave 10 efficient.

As shown in FIG. 3, the transparent substrate 24 is necessary to provide the semiconductor 23, the insulator 22 and the material-sensitive film 21. Furthermore, the transparent substrate 24 is also necessary to maintain mechanical strength of the material detecting plate 5. In this embodiment, sapphire is used as the transparent substrate 24. As shown in FIGS. 3 and 4, the semiconductor 23 is arranged on the upper side of the transparent substrate 24, the insulator 22 is arranged on the upper side of the semiconductor 23, and the material-sensitive film 21 is arranged on the upper side of the insulator 22.

As shown in FIG. 4, the pulsed laser beam 9 is irradiated from the side of the material detecting plate 5 opposite to the surface on which the material-sensitive film 21 is provided. Then, as the semiconductor provided on the material detecting plate 5, a semiconductor film (semiconductor 23) is provided on an insulator substrate through which the pulsed laser beam 9 can be transmitted (transparent substrate 24).

As shown in FIG. 3, a lead wire 25 is electrically connected to the semiconductor 23 so as to apply voltage on the semiconductor 23 at need. Accordingly, the width of the depletion layer in the semiconductor 23 can be controlled.

By providing a protective film of silicone nitride or the like on the insulator 22, ions in the solution are prevented from percolating into the insulator 22 so as to make the detection signal unstable.

As shown in FIGS. 4 and 5, in the material detecting plate 5, the plate-like flow passage forming part 6 is laminated integrally on the material-sensitive film 21. The flow passage 12 which is crank-like when viewed in side is provided inside the flow passage forming part 6, and the flow passage 12 is square in section (see FIG. 5). The bottom which is a part of the flow passage 12 is formed by the surface of the material-sensitive film 21. An interface S between the material-sensitive film 21 and the flow passage faulting part 6 is closely sealed except for the part of the material-sensitive film 21 forming the bottom of the flow passage 12, and an interface between the flow passage forming part 6 and the insulator 22 is closely sealed similarly, whereby the solution is prevented from infiltrating from the flow passage 12 into the interface S. Namely, in the case that the solution flows in the flow passage 12 or is pooled in the flow passage 12, the solution touches the surface of the material-sensitive film 21 which is the bottom of the flow passage 12. The shape of the flow passage 12 is not limited to be crank-like especially, and may be changed suitably corresponding to the type of welding reaction or the like. For example, the shape of the flow passage may be straight, meandering or Y-like. The flow passage forming part 6 may be constructed with a heating or cooling means provided in the vicinity of the flow passage 12.

As shown in FIG. 4, the solution including the material to be detected is injected through a solution inlet 32, and the solution disused after the inspection is discharged through a solution outlet 33.

As shown in FIG. 6, a reference electrode 26 which is means for stabilizing the electric potential of the solution is interposed to a predetermined position at a middle of a solution supply pipe connected to the solution inlet 32. The reference electrode 26 is a silver-silver chloride electrode soaked in saturated potassium chloride solution, and is constructed that the silver-silver chloride electrode is put in a glass pipe in which the saturated potassium chloride solution is enclosed. A voltage source is arranged between the reference electrode 26 and the lead wire 25 so as to apply voltage and functions as means for stabilizing the solution including the material to be detected.

The solution concentration distribution measuring device 1 is constructed as the above, and the material to be detected included in the solution is measured as mentioned below.

As shown in FIG. 1, the measurement plate 20 is arranged on a predetermined position of the scanning table 7. By the control of the controlling and analyzing unit 8, the measurement plate 20 is moved on the scanning table 7 so as to make the irradiated position of the pulsed laser beam 9 in agreement with a predetermined position (start position) of the material-sensitive film 21 which is the bottom of the flow passage 12.

Then, the controlling and analyzing unit 8 makes the pulsed laser source 2 irradiate the pulsed laser beam 9 to a position which is opposite to the insulator 22 in the semiconductor 23 of the material detecting plate 5 and corresponds to the material-sensitive film 21. The pulsed electromagnetic wave 10 generated by the irradiation of the pulsed laser beam 9 is detected by the detecting and exchanging unit 4, and the controlling and analyzing unit 8 captures the detection result so as to detect existence of reaction in the material-sensitive film 21 and degree of the reaction based on the amplitude strength of the pulsed electromagnetic wave 10.

While continuing the detection of the pulsed electromagnetic wave 10 about the material-sensitive film 21, the controlling and analyzing unit 8 controls the scanning table 7 for moving the measurement plate 20 so as to irradiate the pulsed laser beam 9 to the semiconductor 23 corresponding to the material-sensitive film 21 in the flow passage 12. As mentioned above, in the solution concentration distribution measuring device 1, the means for scanning two-dimensionally and irradiating the pulsed laser beam 9 (scanning table 7, pulsed laser source 2) is provided, and the means for scanning two-dimensionally and irradiating the pulsed laser beam 9 (scanning table 7, pulsed laser source 2) irradiates the pulsed laser beam 9 continuously to the material-sensitive film 21 (semiconductor 23) so that the amplitude strength of the pulsed electromagnetic wave 10 generated by the irradiation is measured continuously.

Based on the amplitude strength of the pulsed electromagnetic wave 10, the controlling and analyzing unit 8 functions as means for measuring the material to be detected qualitatively or quantitatively so as to obtain reaction distribution or concentration distribution of the material in the solution in the flow passage 12, and detects existence of reaction in each material-sensitive film 21 (existence of change of the electromagnetic wave amplitude strength) and the degree of reaction (change amount of electromagnetic wave amplitude strength) and, based on the detection results, detects the reaction distribution or the concentration distribution in the solution so as to analyze the material to be detected.

An example of measurement of the material to be detected with the solution concentration distribution measuring device 1 is shown in FIG. 7. In FIG. 7, the solution is pooled in the crank-like flow passage 12 shown in FIG. 4 and pH concentration distribution in the solution is mapped two-dimensionally. The left side of the crank-like concentration map shown in FIG. 7(*a*) is the area in which pH is 2 (the area of low concentration solution shown with La), and the right side thereof is the area in which pH is 12 (the area of high concentration solution shown with Ha). When the solution is left to stand for a little while and then stirred (after stirring), the area of high concentration (high pH) is expanded laterally.

In the case that (a) only air, (b) solution about pH2 ($H^+$ concentration: $1.0\times10$-$2.09$ mol/L), and (c) solution about pH11 ($H^+$ concentration: $1.0\times10$-$11.60$ mol/L) are respectively supplied to the flow passage 12 and the concentration distribution is measured with the solution concentration distribution measuring device 1 of the present invention, as shown by comparing (a) only air, (b) solution about pH2 and (c) solution about pH11 shown in FIG. 8 with each other, the concentration distribution changes corresponding to each hydrogen ion concentration and can be measured quantitatively. Accordingly, with the solution concentration distribution measuring device 1 of the present invention, the reaction distribution and concentration distribution of the solution in the flow passage 12 can be measured quantitatively and continuously.

In the analysis of the material to be detected as the above, as mentioned above, the amplitude strength of the pulsed electromagnetic wave 10 changes corresponding to the existence of reaction in the material-sensitive film 21. Accordingly, the existence of the material to be detected is detected based on the existence of the change of amplitude strength of the pulsed electromagnetic wave 10 and two-dimensional mapping of the vicinity of the flow passage 12 is performed, whereby the reaction distribution of the solution can be analyzed.

As mentioned above, pH of the solution is changed by the decomposition of the material to be detected by the material-sensitive film 21 so as to change the amplitude strength of the generated pulsed electromagnetic wave 10. Accordingly, based on the magnitude of change of amplitude strength of the pulsed electromagnetic wave 10, the concentration of the material to be detected is measured and two-dimensional mapping of the vicinity of the flow passage 12 is performed, whereby the concentration distribution of the solution can be analyzed.

According to that the correlation between the irradiation time of the pulsed laser beam 9 and the concentration change of the material to be detected is analyzed based on the analysis of the solution concentration distribution, the decomposition speed of the material to be detected and behavior of change of the speed in the material-sensitive film 21 can also be analyzed. For example, reaction process can be analyzed that the decomposition speed at the time of start of reaction is very low and the decomposition speed is raised suddenly after fixed decomposition progresses, and the reaction process can be analyzed real-timely based on the amplitude strength of the pulsed electromagnetic wave 10.

Furthermore, in the above series of analysis, after the measurement plate 20 is set once, the measurement plate 20 is moved with the scanning table 7 and the pulsed laser beam 9 is irradiated continuously so as to analyze the material to be detected in the whole bottom of the flow passage 12, whereby many analysis data can be obtained efficiently with high workability in a short time. The reaction of the material to be detected and the material-sensitive film 21 can be detected directly so that label-free materials can be detected.

In the solution concentration distribution measuring device 1 for measuring the reaction distribution or the concentration distribution of the material in the solution, comprising: the material detecting plate 5 having the insulator 22, the semiconductor 23 which touches one of the end surfaces of the insulator 22 and has predetermined thickness, and the material-sensitive film 21 which touches the other end surface (in FIG. 3, right end surface) of the insulator 22; the flow passage forming part 6 forming the flow passage 12 on the material detecting plate 5; the means for stabilizing the electric potential of the solution; the means for irradiating the femtosecond laser which is the pulsed laser beam 9 from the semiconductor 23 side to the flow passage 12 side; the means for making the pulsed laser beam 9 scan the material detecting plate 5 two-dimensionally; the means for measuring the amplitude strength of the pulsed electromagnetic wave 10 generated by irradiating the femtosecond laser to the material detecting plate 5; and the means for measuring the material to be detected qualitatively or quantitatively based on the amplitude strength so as to obtain the reaction distribution or the concentration distribution of the material in the solution in the flow passage 12 as the two-dimensional map, wherein the material-sensitive film 21 constitutes a part of the inner wall of the flow passage 12. Accordingly, by irradiating the femtosecond laser which is the pulsed laser beam 9 to the material detecting plate 5 corresponding to the material-sensitive film 21 (measurement part) constituting the part of the flow passage 12, the pulsed electromagnetic wave 10 having the amplitude strength depending on the amount the material in the solution in the flow passage 12 corresponding to the irradiated position efficiently. By measuring the amplitude strength, qualitative evaluation or quantitative evaluation detecting the existence of the material to be detected can be performed. The material at optional position in the flow passage 12 can be measured with high resolution. Accordingly, the continuous measurement of the whole flow passage 12 (two-dimensional mapping of measured value) is enabled, whereby the analysis data of the reaction distribution or the concentration distribution of the material in a short time efficiently. The solution reaction and concentration distribution in a micro flow passage or TAS (Total Analysis System) can be detected non-destructive, non-contactly and real-timely.

Next, for examining in detail relation between spatial resolution of the reaction distribution or the concentration distribution of the material (hereinafter, referred to as contrast) obtained by using the material detecting plate 5 (sensing plate) and terahertz wave radiation intensity which is the amplitude strength of the pulsed electromagnetic wave 10, electric field distribution simulation in the sectional direction of the material detecting plate 5 is performed. The details thereof are explained below.

As shown in FIG. 16, the construction of the material detecting plate 5 is a sapphire substrate which is the transparent substrate 24 (thickness: 600 μm)/the semiconductor 23 (predetermined thickness: L)/the insulator 22, and a solution to be measured M, which is a measured object and includes water solution, exists on the insulator 22. Furthermore, it is supposed that 1000 of hydrogen ion group ($H^+$) adheres to two positions of the surface of the insulator 22 for an interval of 1 μm. Then, distribution of electric field generated by the hydrogen ion group about the predetermined thickness L of the semiconductor 23 is examined in detail. FIGS. 9 to 15 are results of the electric field distribution simulation respectively with the material detecting plate 5 in the cases that the thickness L of the semiconductor 23 is 100, 150, 200, 400, 600, 650 and 1000 nm.

FIG. 9 shows the result in the case that the thickness L of the semiconductor 23 is 1000 nm. The electric field strength is high in the part in the semiconductor 23 layer and indicated with gradation, and the electric field in the semiconductor 23 indicates an area C in which the terahertz wave can be generated.

In this case, the electric fields generated by the hydrogen ion groups of the two positions are connected to each other (the part enclosed with a dotted line in FIG. 9). This indicates that it is difficult to divide two groups as the terahertz wave strength distribution.

Namely, in the case that the thickness L of the semiconductor 23 is 1000 nm, the contrast is not enough to detect the two groups of hydrogen ion adhering for the interval of 1 μm as the electric field distribution (concentration distribution) (the spatial resolution is more than 1 μm). Then, in the case that the thickness L of the semiconductor 23 is 1000 nm in the material detecting plate 5 of this embodiment, the measurement of material with high resolution (the spatial resolution: not more than 1 μm) is difficult.

FIG. 10 shows the result in the case that the thickness L of the semiconductor 23 is 650 nm. In the area C in which the terahertz wave can be generated, the part that the electric fields generated by the hydrogen ion groups of the two positions are connected to each other is smaller than that of the result of L=1000 nm (the part enclosed with a dotted line in FIG. 10).

FIG. 11 shows the result in the case that the thickness L of the semiconductor 23 is 600 nm. Compared with the result of L=650 nm, the electric fields generated by the two hydrogen ion groups are separated more clearly (the part enclosed with a dotted line in FIG. 11).

FIGS. 12 and 13 show the results in the cases that the thickness L of the semiconductor 23 is 400 nm and 200 nm respectively. In the semiconductor 23 layer, the electric fields are separated completely (the parts enclosed with dotted lines in FIGS. 12 and 13), whereby the contrast can be improved by reducing thickness L of the semiconductor 23.

FIGS. 14 and 15 show the results in the cases that the thickness L of the semiconductor 23 is 150 nm and 100 nm respectively. In the semiconductor 23 layer, the electric fields are separated completely (the parts enclosed with dotted lines in FIGS. 14 and 15).

Next, the above-mentioned results of the electric field distribution simulation are described in the light of terahertz wave radiation strength.

In the case of L=650 nm or 600 nm, the whole area in which the electric field is generated is inside the semiconductor 23 layer (the electric field is not leaked to the substrate 24), and the whole electric field generated inside the semiconductor 23 layer contributes to the generation of the terahertz wave which is the pulsed electromagnetic wave 10. However, when the thickness L of the semiconductor 23 is reduced, the electric field is leaked to the substrate 24 so that the terahertz wave generatable area C, that is, the area in the semiconductor 23 layer in which the electric field is generated is reduced. Then, in the case of L=100 nm, almost all the electric field cannot be used for generating the terahertz wave. Practically, as shown in FIG. 16, the terahertz wave is generated at the time that a laser beam from the side of the substrate 24 (an arrow In. in FIG. 16) reaches the terahertz wave generatable area C in the semiconductor 23 layer opposite via the insulator 22 to the solution to be measured M. In this case, after reaching the semiconductor 23 layer, the laser beam is attenuated depending on the optical infiltration length as a curve D shown in FIG. 16 typically. Namely, the extent of the terahertz wave generatable area C (width in the thickness direction of the semiconductor 23 and the like) depends on dielectric constant, thickness and ion charge amount of each of the semiconductor 23 and the insulator 22 (a part F in FIG. 16), and the strength of the laser beam depends on the infiltration length. Accordingly, the strength of the terahertz wave is indicated by the product of the electric field strength of the terahertz wave generatable area C and the strength of the laser beam reaching the point.

FIG. 17 is a graph of relation between the thickness L of the semiconductor 23 and the contrast and the terahertz wave strength according to the above consideration. In FIG. 17, the axis of abscissa indicates the thickness L (nm) of the semiconductor 23, the axis of ordinate (right) indicates the contrast (optional unit), and the axis of ordinate (left) indicates the terahertz strength (optional unit). In this case, the optical infiltration length is supposed to be 1 μm. As shown in FIG. 17, the optimum value in the light of the contrast (spatial resolution) is different from the optimum value in the light of the terahertz strength. In FIG. 18, the product of the contrast about the thickness L of the semiconductor 23 and the terahertz wave strength about the thickness L of the semiconductor 23 according to the relation between the thickness L of the semiconductor 23 and the contrast and the terahertz wave strength so as to estimate the optimum range of the thickness L of the semiconductor 23. In FIG. 18, the axis of abscissa indicates the thickness L (nm) of the semiconductor 23, the axis of ordinate indicates the product of the terahertz strength and the contrast (optional unit). Accordingly, the thickness L of the semiconductor 23 is optimum in the range between about 200 nm and about 600 nm (an area H in FIG. 18). Namely, the optimum range of the thickness L of the semiconductor 23 is within the area of thickness of the semiconductor 23 determined based on the relation of the product of the terahertz wave strength which is the pulsed electromagnetic wave 10 about the thickness L of the semiconductor 23 and the contrast of the electric field distribution indicating the reaction distribution or the concentration distribution about the thickness L of the semiconductor 23, and the determined thickness area of the semiconductor is in the thickness area H of the semiconductor 23 corresponding to a range between a first inflection point 30 and a second inflection point 31 on a curve indicating the relation of the product of the terahertz wave strength about the thickness L of the semiconductor 23 and the spatial resolution of electric field distribution about the thickness L of the semiconductor 23 (curve G in FIG. 18).

According to FIG. 10 (L=650 nm) and FIG. 14 (L=150 nm), out of the thickness area H of the semiconductor 23, the detection accuracy (performance) is reduced (in this embodiment, the spatial resolution becomes more than but the measurement can be performed corresponding to the desired detection accuracy.

The optimum range is determined based on dielectric constant of the semiconductor 23 and the insulator 22, the thickness of the insulator 22 and the kind of the adhering ion, and the present invention is not limited to the value of the above-mentioned simulation.

The "inflection point" herein is a point at which a curve changes convexly (projectingly) and includes a generalized inflection point.

Namely, the predetermined thickness of the semiconductor 23 is within the thickness area H of the semiconductor 23 determined based on the relation of the product of the terahertz wave strength which is the pulsed electromagnetic wave 10 about the thickness of the semiconductor 23 and the spatial resolution which is the minimum interval detectable by resolving the material in the solution on space coordinates as the reaction distribution or the concentration distribution about the thickness of the semiconductor 23. Accordingly, the thickness L of the semiconductor 23 is considered based on not only the amplitude strength of the pulsed electromagnetic wave 10 but also the spatial resolution of the reaction distribution or the concentration distribution of the material in the measured solution, whereby the measurement accuracy of the solution concentration distribution measuring device 1 can be maintained and the thickness of the semiconductor 23 can be optimized so as to secure the spatial resolution.

The determined thickness area H of the semiconductor 23 corresponds to the range between the first inflection point 30 and the second inflection point 31 on the curve G indicating the relation of the product of the terahertz wave strength which is the pulsed electromagnetic wave 10 about the thickness of the semiconductor 23 and the spatial resolution which is the minimum interval detectable by resolving the material in the solution on space coordinates as the reaction distribution or the concentration distribution about the thickness of the semiconductor 23. Accordingly, the thickness L of the semiconductor 23 is considered based on not only the amplitude strength of the pulsed electromagnetic wave 10 but also the spatial resolution of the reaction distribution or the concentration distribution of the material in the measured solution, whereby the measurement accuracy of the solution concentration distribution measuring device 1 can be maintained and the thickness of the semiconductor 23 can be optimized so as to secure the spatial resolution. As shown in the above-mentioned electric field distribution simulation, the measurement of the reaction distribution or the concentration distribution of the material can be performed with high resolution (not more than 1 μm).

The present invention is not limited to the above-mentioned embodiment, and various changes may be performed based on the purport of the present invention and the changes are not excluded from the scope of the present invention.

INDUSTRIAL APPLICABILITY

According to the present invention, a device can be realized which detects interacting reaction between biological materials (antigen-antibody reaction, enzyme reaction, allergic reaction etc.) with high throughput. As the application field, it is applicable widely to clinical examination, tailor-made medical care, medical research, pharmaceutical development, pollution evaluation, food safety management, agricultural chemical inspection etc.

The invention claimed is:

1. A solution concentration distribution measuring device for measuring reaction distribution or concentration distribution of a material in a solution, comprising:
    a material detecting plate including:
        an insulator;
        a semiconductor which touches one of end surfaces of the insulator and has predetermined thickness; and
        a material-sensitive film which touches the other end surface of the insulator;
    a flow passage forming part which forms a flow passage of the solution on the material detecting plate;
    means for stabilizing electric potential of the solution;
    means for irradiating a femtosecond laser from the semiconductor side to the flow passage side;
    means for making the femtosecond laser scan the material detecting plate two-dimensionally;
    means for measuring directly amplitude strength of a pulsed electromagnetic wave generated by irradiating the femtosecond laser to the material detecting plate with the means for the two-dimensional scanning; and
    means for measuring the material to be detected qualitatively and quantitatively based on the amplitude strength so as to obtain the reaction distribution or the concentration distribution of the material in the solution in the flow passage as a two-dimensional map,
    wherein the material-sensitive film constitutes a part of an inner wall of the flow passage, and the predetermined thickness of the semiconductor is optical infiltration length which is an inverse of optical absorption coefficient of the semiconductor.

2. A solution concentration distribution measuring device for measuring reaction distribution or concentration distribution of a material in a solution, comprising:
    a material detecting plate including:
        an insulator;
        a semiconductor which touches one of end surfaces of the insulator and has predetermined thickness; and
        a material-sensitive film which touches the other end surface of the insulator;
    a flow passage forming part which forms a flow passage of the solution on the material detecting plate;
    means for stabilizing electric potential of the solution;
    means for irradiating a femtosecond laser from the semiconductor side to the flow passage side;
    means for making the femtosecond laser scan the material detecting plate two-dimensionally;
    means for measuring directly amplitude strength of a pulsed electromagnetic wave generated by irradiating the femtosecond laser to the material detecting plate with the means for the two-dimensional scanning; and
    means for measuring the material to be detected qualitatively and quantitatively based on the amplitude strength so as to obtain the reaction distribution or the concentration distribution of the material in the solution in the flow passage as a two-dimensional map,
    wherein the material-sensitive film constitutes a part of an inner wall of the flow passage, and
    the predetermined thickness of the semiconductor is within a thickness area of the semiconductor determined based on relation of product of amplitude strength of the pulsed electromagnetic wave about the thickness of the semiconductor and spatial resolution which is the minimum interval detectable by resolving the material in the solution on space coordinates as the reaction distribution or the concentration distribution about the thickness of the semiconductor.

3. The solution concentration distribution measuring device according to claim 2, wherein the determined thickness area of the semiconductor corresponds to a range between a first inflection point and a second inflection point on a curve indicating the relation of the product of the pulsed electromagnetic wave about the thickness of the semiconductor and the spatial resolution which is the minimum interval detectable by resolving the material in the solution on space coordinates as the reaction distribution or the concentration distribution about the thickness of the semiconductor.

\* \* \* \* \*